United States Patent [19]

Sabahi et al.

[11] Patent Number: 5,240,630
[45] Date of Patent: Aug. 31, 1993

[54] REFRIGERATION COMPOSITIONS CONTAINING DIESTER-AMIDES OF DIALKANOLAMINES

[75] Inventors: Mahmood Sabahi, Baton Rouge, La.; Donald R. Bell, Collinsville, Ill.

[73] Assignee: Ethyl Corporation, Richmond, Va.

[21] Appl. No.: 958,628

[22] Filed: Oct. 9, 1992

Related U.S. Application Data

[63] Continuation-in-part of Ser. No. 760,598, Sep. 16, 1991, abandoned.

[51] Int. Cl.$^5$ .................... C10M 105/68; C09K 5/04
[52] U.S. Cl. ........................................ 252/68; 252/67; 252/51.5 A; 554/112; 560/252
[58] Field of Search ............ 252/68, 67, 51.5 A; 554/112; 560/252

[56] References Cited

U.S. PATENT DOCUMENTS

| | | | |
|---|---|---|---|
| 3,179,615 | 4/1965 | Magne et al. | 560/252 |
| 3,211,766 | 10/1965 | Magne et al. | 560/252 |
| 4,208,293 | 6/1980 | Zaweski | 252/51.5 A |
| 4,992,188 | 2/1991 | Jolley | 252/51.5 A |

FOREIGN PATENT DOCUMENTS 1114508 10/1961 Fed. Rep. of Germany .
989009 4/1965 United Kingdom .

*Primary Examiner*—Christine Skane
*Attorney, Agent, or Firm*—Patricia J. Hogan

[57] ABSTRACT

A refrigeration lubricant suitable for use with R-134a-type refrigerants comprises at least one dialkanolamine diester-amide oil corresponding to one of the formulas:

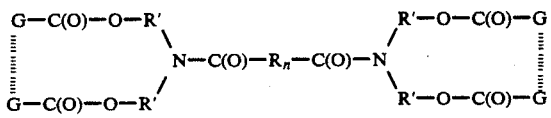

and

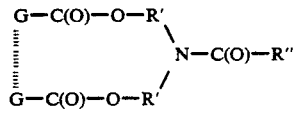

in which formulas R is a hydrocarbylene group containing 1-10 carbons; n represents zero or one; each R' is independently selected from alkylene groups containing 1-10 carbons; R" is hydrogen or a hydrocarbyl group containing 1-10 carbons; and each G, when not linked with another G, is independently selected from hydrocarbyl groups containing 1-10 carbons or, when linked with another G, is a hydrocarbylene group which, together with the colinked G, forms a hydrocarbylene group containing 1-10 carbons.

15 Claims, No Drawings

REFRIGERATION COMPOSITIONS CONTAINING DIESTER-AMIDES OF DIALKANOLAMINES

CROSS-REFERENCE TO RELATED APPLICATION

This application is a continuation-in-part of copending application Ser. No. 07/760,598, filed Sep. 16, 1991 now abandoned.

FIELD OF INVENTION

The invention relates to refrigeration compositions and more particularly to such compositions containing diester-amides of dialkanolamines as lubricants.

BACKGROUND

Many natural and synthetic materials are known to be useful as lubricants, their utility in particular applications depending on factors such as their stability and viscosity under the conditions of use, their pour points, and their compatibility with any materials with which they will be used.

In refrigeration applications (e.g., home-use or industrial-use refrigerators, freezers, or air conditioners for buildings, automobiles, airplanes, and other vehicles), the need to replace chlorofluorocarbon refrigerants with a refrigerant having lesser ozone-depleting potential has made it important to find lubricants which would be suitable for use with 1,1,1,2-tetrafluoroethane (R-134a), a refrigerant that has been reported to have an ozone depletion potential of zero. Mineral oils, usually the refrigeration lubricants of choice in the past, cannot be utilized in this application because of incompatibility with R-134A.

Jolley, "New and Unique Lubricants for Use in Compressors Utilizing R-134a Refrigerant," pp. 145–152 (a paper presented at the ASHRE/Refrigeration/Compressor Engineering Conference at Purdue, July 1990), reports that preliminary tests conducted on certain esters, amides, and polyalkyleneglycols indicated that fluids of such types held the greatest promise of providing acceptable fluids for use as compressor lubricants in refrigeration applications utilizing R-134A. U.S. Pat. No. 4,992,188 (Jolley-A) indicates that the amides subjected to those preliminary tests were tertiary amides of the type obtained by reacting (1) a hydrocarbylpolyoxyalkylenealkanoic acid or (2) a hydrocarbyl mono- or dicarboxylic acid or anhydride with a secondary amine which may be a di(cyclo)alkylamine or a heterocyclic amine (such as pyrrolidines, piperidines, morpholines, and piperazines) that, except for the amino nitrogen, is hydrocarbyl in nature.

As explained in his patent, Jolley prefers his amines to be "purely" hydrocarbylamines, i.e., amines in which the hydrocarbyl groups are true hydrocarbyl groups containing no atoms other than carbon and hydrogen. However, in a less preferred embodiment of his invention, he considers it acceptable to use "substantially" hydrocarbylamines, i.e., amines in which the hydrocarbyl portion(s) contain hetero atoms or non-hydrocarbyl substituents which are of a type and number such that they do not alter the predominantly hydrocarbon nature of the group(s) as they exist in the amines and the tertiary amides produced therefrom.

Both Jolley and Jolley-A indicate that the above-described tertiary amides perform well as refrigeration lubricants when used together with R-134a and similar refrigerants, but they are uneconomical to prepare. Thus, there is still a need for amide-type lubricants which (1) like those of Jolley, would have R-134a compatibility and appropriate viscosities over the entire temperature range to which a refrigeration composition is apt to be exposed but (2) unlike Jolley's amides, could be synthesized from relatively inexpensive starting materials.

U.S. Pat. No. 4,208,293 (Zaweski) discloses amide/ester/diester-amide mixtures which are useful as additives for crankcase oils and can be obtained by reacting diethanolamine with a fatty acid that preferably contains $\geq 8$ carbons, more preferably 8–22 carbons.

British Patent 989,009 (Produits Chimiques) teaches diester-amides of dialkanolamines which are similar to those of Zaweski in that they have the same acid residue in the amide and ester portions of the molecule but are dissimilar to Zaweski's diester-amides both in the smaller carbon content of the acid residues and in the application for which they are intended, i.e., plasticizers for vinyl resins.

U.S. Pat. No. 3,179,615 (Magne et al.) and German Auslegeschrift 1114508 (Chemische Fabrik Düren) teach other diester-amides of dialkanolamines which, like those of Produits Chimiques, have utility as plasticizers but, unlike those of Produits Chimiques and Zaweski, have different acid residues in the amide and ester portions of the molecule. The diester-amides of Magne et al. have monounsaturated and/or epoxidized alkenyl groups of 11–21 carbons as the hydrocarbyl groups in the amide portion and methyl, cyclohexyl, phenyl, or substituted phenyl groups in the ester portions. Düren's diester-amides have residues of lower mono- or dicarboxylic acids, such as formic, acetic, propionic, oxalic, malonic, maleic, or adipic acid, in the amide portion, while their ester portions have residues of higher fatty acids containing 10–24 carbons.

SUMMARY OF INVENTION

It has been found that certain diester-amides of dialkanolamines have excellent compatibility with R-134a and other refrigerants as well as having viscosities appropriate for materials to be used as refrigeration lubricants. Thus, the invention resides in refrigeration compositions comprising a refrigerant and a lubricating amount of at least one dialkanolamine diester-amide oil corresponding to one of the formulas:

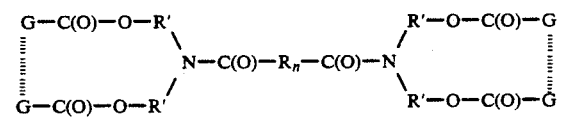

and

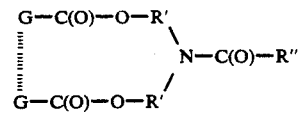

in which formulas R is a hydrocarbylene group containing 1–10 carbons; n represents zero or one; each R' is independently selected from alkylene groups containing 1–10 carbons; R" is hydrogen or a hydrocarbyl group containing 1–10 carbons; and each G, when not linked with another G, is independently selected from hydrocarbyl groups containing 1–10 carbons or, when linked with another G, is a hydrocarbylene group which, together with the colinked G, forms a hydrocarbylene group containing 1–10 carbons.

DETAILED DESCRIPTION

The refrigerants with which the novel lubricants are employed may be one or more of a wide variety of such materials, e.g., ammonia; alcohols such as methanol and ethanol; glycols such as ethylene and propylene glycols; and hydrocarbons such as methane, ethane, propane (R-290), butane, ethylene, and propylene. However, they are more commonly halocarbons and/or halohydrocarbons such as chlorotrifluoromethane, dichlorodifluoromethane, dichlorofluoromethane, chlorodifluoromethane (R-22), 1,2,2-trifluoro-1,1,2-trichloroethane, 1,1-dichloro-2,2,2-trifluoroethane (R-123), 1,1-dichloro-1-fluoroethane, 1-chloro-2,2,2-trifluoroethane, 1-chloro-1,2,2,2-tetrafluoroethane (R-124), 1-chloro-1,1,2,2-tetrafluoroethane, dichloromethane, difluoromethane (R-32), 1,1,2,2,2-pentafluoroethane (R-125) 1,1,2,2-tetrafluoroethane (R-134), 1,1,1,2-tetrafluoroethane (R-134a), 1,1,1-trifluoroethane (R-143a), 1,1-difluoroethane (R-152a). The preferred refrigerants, of course, are the fluorohydrocarbons —especially R-134a—and fluorohydrocarbon mixtures.

Among the refrigerant blends with which the lubricants can be advantageously used are the binary mixtures of R-32 with R-125, R-152a, or R-134a; R-125/R-143a, R-290/R-134a, and R-22/R-152a binary blends; and ternary blends such as R-22/R-290/R-125, R-22/R-152a/R-124, R-32/R-125/R-134a, and R-125/R-143a/R-134a.

In choosing a lubricant for use with any of these refrigerants, it is important to select one which is completely miscible with the refrigerant throughout the temperature range to which the refrigeration composition is to be exposed and which has a viscosity such as to permit its functioning as a lubricant over that entire temperature range. The optimum lubricant to be used in any instance can be determined by routine experimentation, aided by observation of the following general principles:

(1) Miscibility with refrigerants is usually decreased and the viscosity increased as the size of the hydrocarbon groups is increased.

(2) A low viscosity is most suitable for a lubricant to be used at relatively low temperatures, while lubricants intended for use at relatively high temperatures should have higher viscosities.

(3) The viscosities most suitable for lubricants to be used in refrigeration compositions that are to be exposed to the temperature conditions generally found in refrigeration equipment (i.e., temperatures in the range of about $-40°$ C. to $70°$ C. or sometimes even higher temperatures) are apt to be 1–600, preferably 5–300, and most preferably 10–200 $mm^2 \cdot s^{-1}$ at $40°$ C.; and it is frequently also desirable for the lubricant to have a viscosity index $\geq 100$.

The refrigeration lubricants of the invention are diester-amide oils corresponding to either of the above formulas, the first of which represents bis(diester-amides) of the type obtained by reacting one or more dialkanolamines with one or more dicarboxylic acids, anhydrides, or halides to form one or more bisamides and then esterifying the bisamide(s) with one or more monocarboxylic or dicarboxylic acids or anhydrides, and the second of which represents diester-amides of the type produced by reacting one or two dialkanolamines with one or more monocarboxylic acids, anhydrides, or halides to form one or more amides and then esterifying the amide(s) with one or more monocarboxylic or dicarboxylic acids or anhydrides.

Dialkanolamines utilizable in preparing the diester-amides are those containing 1–10 carbons in the hydroxyalkyl groups, such as dimethanolamine, diethanolamine, dipropanolamine, dibutanolamine, dipentanolamine, dihexanolamine, diheptanolamine, dioctanolamine, dinonanolamine, didecanolamine, N-hydroxymethyl-N-hydroxyethylamine, N-hydroxyethyl-N-hydroxyproplyamine, N-hydroxyethyl-N-hydroxybutylamine, N-hydroxyethyl-N-hydroxydecylamine, N-hydroxypropyl-N-hydroxybutylamine, and the like. Although diethanolamine, dipropanolamine, and mixtures thereof are ordinarily preferred because of availability and cost, any of the other dialkanolamines or dialkanolamine mixtures can sometimes be preferred to achieve different viscosities.

The carboxylic compounds with which the dialkanolamines are reacted to form the amide intermediates, as well as those with which the intermediates are esterified to form the diester-amides, may be monocarboxylic or dicarboxylic acids or their derivatives, like the anhydrides or acid halides. In general, they are saturated or unsaturated, straight-chain or branched-chain aliphatic, cycloaliphatic, or aromatic acids or derivatives that have a moiety which is at least substantially hydrocarbon in nature and contains 1–10 carbons and not more than one hetero atom (e.g., sulfur, oxygen, or nitrogen) or non-hydrocarbon substituent (e.g., halo, hydroxy, alkoxy, mercapto, alkylmercapto, nitro, nitroso, or sulfoxy group) per five carbons in the substantially hydrocarbon moiety. As indicated by the above formulas, however, formic and oxalic acids are also useful as carboxylic reactants in the preparation of the amide intermediates.

The more preferred carboxylic compounds are the acids, anhydrides, and halides wherein the hydrocarbon moieties are pure hydrocarbon groups containing 1–10, most preferably 2–8 carbons. Exemplary of these compounds are (cyclo)aliphatic acids such as acetic, propionic, butyric, isobutyric, pentanoic, hexanoic, cyclohexanoic, heptanoic, isoheptanoic, octanoic, isooctanoic, 2-ethylhexanoic, nonanoic, isononanoic, decanoic, isodecanoic, undecanoic, malonic, succinic, glutaric, adipic, pimelic, suberic, azelaic, sebacic, brassic, dodecanedioc, maleic, and fumaric acids and the corresponding anhydrides and acid halides; and aromatic acids such as phthalic, isophthalic, and terephthalic acids and the corresponding anhydrides and acid halides. The most preferred carboxylic compounds are generally the alkanoic acids.

Although, for the most part, the carboxylic compounds utilizable in preparing the amides and those useful in esterifying the amides to the diester-amides may be the same, it is ordinarily preferred to use a mixture of two or more different carboxylic compounds in the amidation reaction and/or to esterify the amides with one or more carboxylic compounds different from those employed in the amidation reaction in order to provide a diester-amide or mixture of diester-amides containing a good balance of acidic moieties that enhance compatibility with refrigerant sand acidic moieties that contribute improved viscosities.

The preparation of the diester-amides is most commonly achieved by (1) reacting a first carboxylic compound or mixture of carboxylic compounds with the dialkanolamine(s) in a molar ratio of about 0.8–3/1, preferably about 1–3/1, and most preferably about 1/1 when using monocarboxylic acids or a molar ratio of about 1.6–6/1, preferably about 2–6/1, and most preferably about 2/1 when using dicarboxylic acids to form an intermediate which may contain some ester but is predominantly amide, (2) esterifying the intermediate with a stoichiometric excess of a second carboxylic compound or mixture of carboxylic compounds, and (3) recovering the product. Alternatively, the diester-amides may be prepared by reacting all of the reactants (i.e., the dialkanolamine(s) and the amidating and esterifying carboxylic compounds) simultaneously.

After being recovered, the product may be blended with a refrigerant to form a refrigeration composition. Refrigeration compositions of the invention typically comprise 0.001–1, preferably 0.01–0.7, and most preferably 0.1–0.5 part of the novel lubricant per part by weight of the refrigerant; and, if desired, they may also contain additives of the type conventionally used in refrigeration lubricants. In addition to epoxy and other dehydrating agents sometimes employed to prevent corrosion of refrigeration equipment by any water in the refrigeration compositions, such additives include, e.g., oxidation resistance and thermal stability improvers, corrosion inhibitors, metal deactivators, lubricity additives, viscosity index improvers, pour and/or floc point depressants, detergents, dispersants, antifoaming agents, anti-wear agents, and extreme pressure resistance additives, such as those exemplified in Jolley-A and in U.S. Pat. No. 5,021,179 (Zehler et al.), the teachings of both of which are incorporated herein by reference. As in Zehler et al., these additives, when employed, are generally utilized in small amounts totalling not more than 8%, preferably not more than 5%, of the weight of the lubricant formulation.

The refrigeration compositions are generally formed prior to use. However, when desired, they may also be formed in situ during operation of the refrigeration equipment. Thus, the refrigerant and the lubricant may be charged to the refrigeration equipment separately, either simultaneously or consecutively in either order, instead of being preblended.

Although the invention is advantageous in its provision of refrigeration compositions containing other refrigerants, its greatest value is in its ability to provide refrigeration compositions containing lubricants which are suitable for use with refrigerants and refrigerant mixtures that are environmentally superior to the chlorofluorocarbon refrigerants most commonly used in refrigeration applications—especially fluorohydrocarbons such as R-134a. Also, the compositions of the invention are most useful in the various refrigeration systems (such as refrigerators, freezers, and automotive, home, and industrial air conditioners) which are compression-type systems.

The following examples are given to illustrate the invention and are not intended as a limitation thereof.

EXAMPLE 1

Preparation of mixed ester of N,N-bis(2-hydroxyethyl)butyramide

Charge a suitable reaction vessel with 273 g (3.1 mols) of butyric acid and 400 mL of toluene, add 326 g (3.1 mols) of diethanolamine while stirring, and heat the resulting mixture to reflux. Continue refluxing for 20 hours while removing 114 mL of water, and then cool to room temperature. Add 273 g (3.1 mols) of butyric acid, 451 g (3.1 mols) of octanoic acid, and 5 g of methanesulfonic acid as an esterification catalyst to the crude amide in the vessel, and heat the mixture to a temperature sufficient to form an azeotrope of toluene and water. After maintaining the reaction mixture at reflux for eight hours while removing 114 mL of water, cool the mixture to room temperature, wash it twice with equal volumes of distilled water, neutralize it with 10% NaOH solution, wash four times with saturated sodium bicarbonate, and then wash with water again. Dry the organic layer over magnesium sulfate, treat the product with 150 g of neutral alumina, and heat it at 100° C. for three hours under a 0.5 mm Hg vacuum. The product is a bright yellow oil which is totally miscible with R-134a over a temperature range of −40° C. to 70° C. and has a viscosity of 22.9 mm$^2\cdot$s$^{-1}$ at 40° C., a viscosity of 4.41 mm$^2\cdot$s$^{-1}$ at 100° C., a viscosity index of 101, and a total acid number (TAN) of 0.08 mg KOH/g.

EXAMPLE 2

Preparation of mixed diester of N,N-bis(2-hydroxyethyl)propionamide

Repeat Example 1 except for replacing the butyric acid with 3.1 mols of propionic acid in the amidation reaction and replacing the butyric and octanoic acids with 3.1 mols of pentanoic acid and 3.1 mols of heptanoic acid in the esterification reaction. The product is a bright yellow oil which is totally miscible with R-134a over a temperature range of −40° C. to 70° C. and has a viscosity of 16.8 mm$^2\cdot$s$^{-1}$ at 40° C., a viscosity of 3.47 mm$^2\cdot$s$^{-1}$ at 100° C., and a viscosity index of 69.

What is claimed is:

1. A refrigeration composition comprising a refrigerant and a lubricating amount of at least one dialkanolamine diester-amide oil corresponding to one of the formulas:

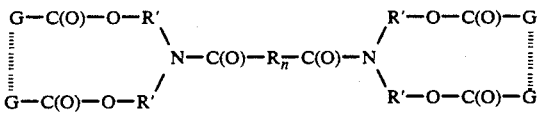

and

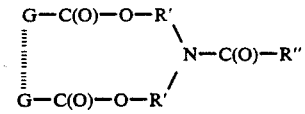

in which formulas R is a hydrocarbylene group containing 1–10 carbons; n represents zero or one; each R' is independently selected from alkylene groups containing 1–10 carbons; R" is hydrogen or a hydrocarbyl group containing 1–10 carbons; and each G, when not linked with another G, is independently selected from hydrocarbyl groups containing 1–10 carbons or, when linked with another G, is a hydrocarbylene group which, together with the colinked G, forms a hydrocarbylene group containing 1–10 carbons.

2. The composition of claim 1 wherein the diester-amide/refrigerant weight ratio is 0.001–1/1.

3. The composition of claim 2 wherein the diester-amide/refrigerant weight ratio is 0.01–0.7/1.

4. The composition of claim 3 wherein the diester-amide/refrigerant weight ratio is 0.1–0.5/1.

5. The composition of claim 1 wherein the refrigerant comprises at least one fluorohydrocarbon.

6. The composition of claim 5 wherein the refrigerant is 1,1,1,2-tetrafluoroethane.

7. The composition of claim 1 wherein the diester-amide corresponds to the formula:

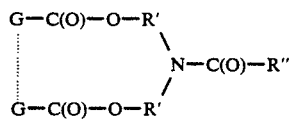

8. The composition of claim 7 wherein the diester-amide is a diester-amide of a dialkanolamine selected from the group consisting of diethanolamine, dipropanolamine, and mixtures thereof.

9. The composition of claim 8 wherein the dialkanolamine is diethanolamine.

10. The composition of claim 7 wherein $R''$ and G are alkyl groups containing 2–8 carbons.

11. The composition of claim 10 wherein $R''$ and each G represent different alkyl groups.

12. The composition of claim 11 wherein the diester-amide is a diester-amide of diethanolamine.

13. The composition of claim 12 wherein the refrigerant comprises at least one fluorohydrocarbon.

14. The composition of claim 13 wherein the refrigerant is 1,1,1,2-tetrafluoroethane.

15. The composition of claim 14 wherein the diester-amide/refrigerant weight ratio is 0.1–0.5/1.

* * * * *